United States Patent [19]
Ainsworth et al.

[11] Patent Number: 5,554,121
[45] Date of Patent: Sep. 10, 1996

[54] INTRALUMINAL CATHETER WITH HIGH STRENGTH PROXIMAL SHAFT

[75] Inventors: Robert D. Ainsworth, Scotts Valley; Tai C. Cheng, Mountain View; Lawrence D. Wasicek, Sunnyvale, all of Calif.

[73] Assignee: Advanced Cardiovascular Systems, Inc., Santa Clara, Calif.

[21] Appl. No.: 280,210

[22] Filed: Jul. 25, 1994

[51] Int. Cl.$^6$ ............................................. A61M 29/00
[52] U.S. Cl. ............................. 604/96; 604/97; 604/280
[58] Field of Search ........................... 604/96–103, 280, 604/282; 606/192, 194

[56] References Cited

U.S. PATENT DOCUMENTS

| | | | |
|---|---|---|---|
| 5,139,496 | 8/1992 | Hed | 606/23 |
| 5,176,637 | 1/1993 | Sagae | 604/96 |
| 5,213,574 | 5/1993 | Tucker | 604/93 |
| 5,258,160 | 11/1993 | Utsumi et al. | 264/558 |
| 5,259,839 | 11/1993 | Burns | 604/99 |
| 5,270,086 | 12/1993 | Hamlin | 604/96 X |
| 5,304,134 | 4/1994 | Kraus et al. | 604/96 |
| 5,316,706 | 5/1994 | Muni et al. | 264/25 |
| 5,344,400 | 9/1994 | Kaneko et al. | 604/96 |
| 5,423,754 | 6/1995 | Cornelius et al. | 604/96 |

FOREIGN PATENT DOCUMENTS

| | | |
|---|---|---|
| 0171884 | 2/1986 | European Pat. Off. . |
| 0452595A1 | 10/1991 | European Pat. Off. . |

*Primary Examiner*—John D. Yasko
*Assistant Examiner*—Laird J. Knights
*Attorney, Agent, or Firm*—Crosby, Heafey, Roach & May

[57] ABSTRACT

A balloon dilatation having a relatively stiff proximal catheter shaft which is formed at least in part of an engineering thermoplastic polymer material with a tensile strength of at least about 10,000 psi, an elongation of at least 50% and a tensile modulus of at least 300,000 psi. The polymer is preferably an aromatic polymer, and particularly polyetheretherketone.

6 Claims, 1 Drawing Sheet

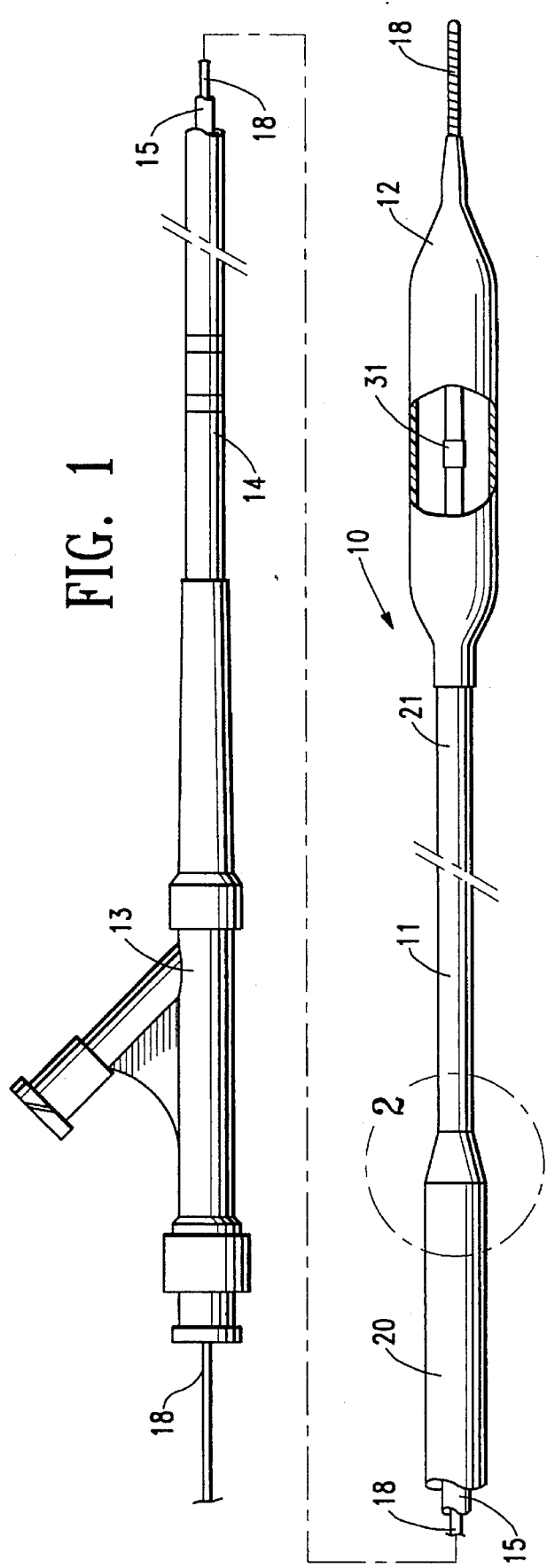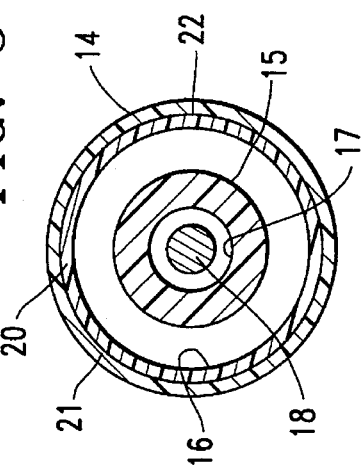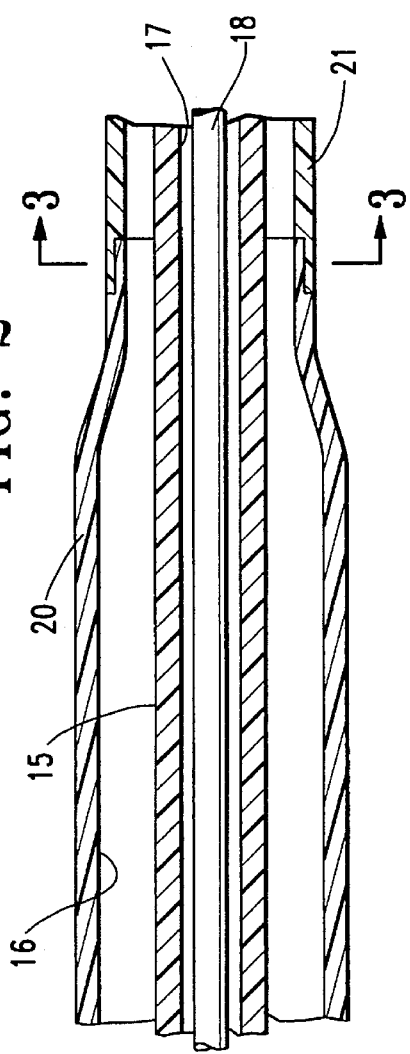

INTRALUMINAL CATHETER WITH HIGH STRENGTH PROXIMAL SHAFT

BACKGROUND OF THE INVENTION

This invention relates to the field of intravascular catheters, and more particularly to a dilatation catheter for percutaneous transluminal coronary angioplasty (PTCA).

PTCA is one of the most widely used treatment modalities for heart disease. The procedure basically comprises advancing a dilatation catheter, having an inflatable balloon on the distal portion thereof, into the patient's coronary anatomy until the balloon of the dilatation catheter is properly positioned across the lesion to be dilated. Once properly positioned, the dilatation balloon is inflated with liquid one or more times to a predetermined size at relatively high pressures (e.g. greater than 4 atmospheres) to expand the arterial passageway. Generally, the inflated diameter of the balloon is approximately the same diameter as the native diameter of the body lumen being dilated so as to complete the dilatation but not overexpand the artery wall. After the balloon is finally deflated, blood flow resumes through the dilated artery and the dilatation catheter can be removed therefrom.

Commercially available over-the-wire dilatation catheters for angioplasty and other vascular procedures usually comprise an elongated shaft with an inflatable dilatation member on a distal portion of the shaft and an adapter on the proximal end of the shaft for the delivery of inflation fluid through an inner lumen extending through the catheter shaft to the interior of the inflatable dilatation member. A second inner lumen configured to slidably receive a guidewire extends through the shaft to a guidewire port in the distal end of the catheter. Conventional over-the-wire catheters have the guidewire receiving inner lumens extending from the proximal end of the catheter to the distal end of the catheter. A catheter configured for rapid exchange has a much shorter guidewire lumen and extends from a proximal guidewire port spaced a substantial distance from the proximal end of the catheter to the distal port in the distal end.

The progression of improvements in dilatation catheters generally has been to make the catheters with lower profiles, i.e. smaller transverse dimensions, and with the stiffer proximal shafts. A stiffened proximal shaft provides greater push to the catheter which facilitates advancement over a guidewire in tortuous anatomy. Stiffened proximal shaft sections formed of plastic materials, stainless steel and superelastic NiTi alloys are disclosed in the prior art. However, the raw material and manufacturing costs for a catheter having a relatively stiff proximal shaft is quite high.

What has been needed is an intralumenal catheter which has a low profile and a relatively stiff proximal shaft which is easy and inexpensive to manufacture. The present invention provides such a desirable product.

SUMMARY OF THE INVENTION

This invention is directed to an intraluminal catheter which has at least part of the shaft thereof formed of a melt processable engineering thermoplastic polymer material and preferably an aromatic polymer. The melt processed, e.g. extruded, thermoplastic polymer has a tensile strength greater than 10,000 psi, preferably greater than 14,000 psi, an elongation at break greater than 50%, preferably greater than 60%, and a tensile modulus greater than 300,000 psi, preferably greater than 400,000 psi. The melt processable linear aromatic polymers including polyetheretherketone (PEEK), polyetherketone, polyketone, polyethereketoneketone, polyaryletherketone, polysulfone and polyether sulfone. Other aromatic engineering thermoplastic polymers which have the above properties are also suitable.

One presently preferred embodiment of the invention is a dilatation catheter which has an elongated catheter shaft with a relatively stiff proximal portion formed of the engineering thermoplastic polymer and a relatively flexible distal portion and an inflatable dilatation member on the distal portion of the catheter. The proximal portion of the presently preferred embodiment has an outer tubular member, an inner tubular member disposed within the outer tubular member and defining an annular inner lumen between the inner and outer tubular member. The inner tubular member has an inner lumen which extends to a distal guidewire port in the distal end thereof. At least one of the inner and outer tubular members forming the proximal portion of the catheter shaft are formed of the engineering thermoplastic polymer described above.

In this embodiment, the distal portion of the inflatable dilatation member is sealed about and secured to a distal extremity of the inner tubular member and the proximal portion of the inflatable dilatation member is sealed about and secured to a distal extremity of the outer tubular member.

The intraluminal catheter of the invention has excellent pushability due to the relatively stiff proximal portion, yet because the requisite aromatic polymers can be formed into very thin walled structures and have relatively high strength and elongation properties, the catheter shafts generally do not kink under normal intraluminal use. These and other advantages of the invention will become more apparent from the following detailed description of the invention and the accompanying exemplary drawings.

BRIEF DESCRIPTION OF THE DRAWINGS

FIG. 1 is an elevational view partially in section of a dilatation catheter assembly which embodies features of the invention.

FIG. 2 is a longitudinal cross-sectional view of the shaft of the catheter assembly shown in circle 2 shown in FIG. 1.

FIG. 3 is a transverse cross-sectional view of the shaft shown in FIG. 2, taken along the lines 3—3.

DETAILED DESCRIPTION OF THE INVENTION

As shown in FIG. 1 the dilatation catheter 10 of the invention generally includes an elongated catheter shaft 11 with an inflatable dilatation balloon 12 on a distal portion of the catheter shaft and an adapter 13 mounted on the proximal end of the catheter shaft.

The catheter shaft 11 has an outer tubular member 14 and an inner tubular member 15 disposed within the outer tubular member and defining with the outer tubular member annular lumen 16 which is in fluid communication with the interior of the inflatable dilatation balloon 12. The inner tubular member 15 has an inner lumen 17 extending therein which is configured to slidably receive a guidewire 18 suitable for advancement through a patient's coronary arteries.

The distal extremity of the inflatable dilatation balloon 12 is sealingly secured to the distal extremity of the inner tubular member 15 and the proximal extremity of the balloon is secured to the distal extremity of the outer tubular member 16.

The outer tubular member 16 has a relatively stiff proximal portion 20 formed of a requisite linear aromatic polymer and the distal extremity of the proximal portion 20 is secured to the proximal extremity of the distal portion 21 of the outer tubular member at a lap joint 22 formed by suitable means such as heat or laser fusion or commercially available cyanoacrylate adhesives. The distal portion 21 of the outer tubular member 14 is formed of a melt processable more flexible polymer material such as polyethylene or Hytrel®. The inner tubular member 15 extends along the entire length of the catheter and may be formed of suitable materials such as polyethylene, Hytrel® and the like.

The length of the dilatation catheter 10 may be about 120 to about 150 cm in length, and typically is about 135 cm in length. The outer tubular member 15 has an OD of about 0.03 to about 0.05 inch (0.76–1.27 mm) and an ID of about 0.025 to about 0.035 inch (0.635–0.899 mm). Although not shown in the drawings, the outer tubular member 14 may taper in its distal portion to a smaller OD of about 0.04 to about 0.02 inch (1.02–10.5 mm) and a smaller ID of about 0.03 to about 0.015 inch ((0.762– 0.381). The smaller diameter portion between the taper and the proximal extremity of the balloon 12 may be about 5 to about 25 cm in length.

The inner tubular member 15 has an OD ranging from about 0.018 to about 0.026 inch (0.457–0.66 mm), and the ID of the inner tubular member will usually be determined by the diameter of the guidewire 18 which is to be used with the catheter, which may range from about 0.008 to about 0.02 inch ((0.203–0.51 mm). The inner diameter of the inner lumen should be about 0.002 to about 0.005 (0.051–0.127 mm) inch larger than the OD of the guidewire 18 to be used. Usually there will be a family of catheters for each size of guidewire with a variety of maximum inflated balloon sizes, e.g. 0.5 to about 4 mm in diameter and with various working lengths ranging from about 1 to about 10 cm.

In a presently preferred embodiment the proximal portion 20 of the outer tubular member 16 is formed of PEEK (Grade 381 G) from Victrex USA. The resin is readily extruded at a temperature of about 750° to about 800° F. at a pressure of about 2800 psi into thin walled tubing suitable for the outer tubular member forming the proximal portion of the catheter shaft. The proximal end of the distal portion of the outer tubular member is plasma treated to facilitate the joining of the distal end of the extruded tubular member to the proximal end of the distal portion of the outer tubular member 16. The proximal end of the distal portion 21 of the outer tubular member 16 is secured by a suitable adhesive in a lap joint at least about 1 mm and preferably about 2 to about 4 mm in length to the distal end of the distal portion 21 of the outer tubular member 16. The adhesive is preferably a UV cured adhesive such as UV 350 which is available from the Loctite Corporation, although other conventional adhesives are suitable.

In another preferred embodiment of the invention inner tubular member 15 is preferably of composite construction comprising a polymer such as polyethylene or Hytrel® which has incorporated therein graphite particles, such as described in copending application Ser. No. 08/134,863, filed on Oct. 12, 1993, entitled COMPOSITE MATERIAL HAVING A LUBRICOUS SURFACE FOR CATHETER USE, and application filed concurrently herewith, Ser. No. 08/280,291, filed Jul. 26 1994, now abandoned entitled COMPOSITE POLYESTER MATERIAL HAVING A LUBRICOUS SURFACE, both of which are incorporated herein in their entirety. Both application are assigned or will be assigned to the present assignee, Advanced Cardiovascular Systems, Inc.

To the extent not previously described herein, the various catheter components may be formed of conventional materials. For example, the radiopaque marker 31 may be a gold band and the adapter body may be formed of polycarbonate polymers. The balloon 12 may be a relatively inelastic high strength material such as polyethylene, polyethylene terephthalate, polyolefinic ionomers such as Surlyn®, nylon and the like which are frequently used to form dilatation balloons.

While the present invention has been described herein primarily in terms of a catheter construction wherein the proximal portion of the outer tubular member is formed of the requisite linear aromatic polymer, those skilled in the art will recognize that the proximal portion or the entire inner tubular member may be formed of a linear aromatic polymer. Moreover, a portion of the catheter shaft can have an extruded dual lumen construction which is formed of a linear aromatic polymer. Other modifications and improvements may be made to the invention with out departing from the scope thereof.

What is claimed is:

1. A balloon dilatation catheter comprising:

a) a proximal catheter shaft portion formed at least in part of an extruded engineering thermoplastic polymeric material with a tensile strength greater than 10,000 psi, an elongation greater than 50% and a tensile modulus greater than 300,000 psi, having proximal and distal ends and having a first inner lumen extending therein to the distal end;

b) a distal catheter shaft portion being more flexible than the proximal catheter shaft portion, having proximal and distal ends and a second inner lumen extending from the proximal end of the distal shaft portion to a location proximal to the distal end of the distal catheter shaft portion and being in fluid communication with the first inner lumen extending within the proximal catheter shaft portion; and c) an expandable dilatation balloon on the distal catheter shaft portion having an interior in fluid communication with the second inner lumen extending within the distal shaft portion.

2. The balloon dilatation catheter of claim 1 wherein the polymeric material is a linear aromatic polymer.

3. The balloon dilatation catheter of claim 2 wherein the linear aromatic polymer is selected from the group consisting of polyetheretherketone, polyetherketone, polyketone, polyethereketoneketone, polyaryletherketone, polysulfone and polyether sulfone.

4. The balloon dilatation catheter of claim 1 wherein the polymeric material of the proximal catheter shaft has a tensile strength greater than about 14,000 psi, an elongation greater than about 60% and a tensile modulus greater than about 400,000 psi.

5. The balloon dilatation catheter of claim 1 wherein the proximal catheter shaft portion has an outer tubular member and an inner tubular member which is disposed within the outer tubular member and which defines with the outer tubular member the first inner lumen extending therein, at least one of the inner and the outer tubular members being formed of the extruded engineering thermoplastic polymeric material.

6. The balloon dilatation catheter of claim 1 wherein the relatively stiff proximal catheter shaft portion includes a relatively flexible distal shaft portion.

\* \* \* \* \*

REEXAMINATION CERTIFICATE (3574th)

United States Patent [19]

Ainsworth et al.

[11] B1 5,554,121

[45] Certificate Issued Jul. 14, 1998

[54] INTRALUMINAL CATHETER WITH HIGH STRENGTH PROXIMAL SHAFT

[75] Inventors: Robert D. Ainsworth, Scotts Valley; Tai C. Cheng, Mountain View; Lawrence D. Wasicek, Sunnyvale, all of Calif.

[73] Assignee: Advanced Cardiovascular Systems, Inc., Santa Clara, Calif.

Reexamination Request:
No. 90/004,602, Apr. 9, 1997

Reexamination Certificate for:
Patent No.: 5,554,121
Issued: Sep. 10, 1996
Appl. No.: 280,210
Filed: Jul. 25, 1994

[51] Int. Cl.[6] .................................................. A61M 29/00
[52] U.S. Cl. ............................... 604/96; 604/97; 604/280
[58] Field of Search ........................... 604/96–103, 280, 604/282; 606/192, 194

[56] References Cited

U.S. PATENT DOCUMENTS

| | | | |
|---|---|---|---|
| 5,139,496 | 8/1992 | Hed | 606/23 |
| 5,259,839 | 11/1993 | Burns | 604/99 |
| 5,270,086 | 12/1993 | Hamlin | 428/35.2 |
| 5,316,706 | 5/1994 | Muni et al. | 264/25 |
| 5,344,400 | 9/1994 | Kaneko et al. | 604/96 |
| 5,423,754 | 6/1995 | Cornelius et al. | 604/103 |
| 5,531,715 | 7/1996 | Engelson et al. | 604/265 |
| 5,542,937 | 8/1996 | Chee et al. | 604/280 |

FOREIGN PATENT DOCUMENTS

| | | |
|---|---|---|
| 0 452 595 A1 | 10/1991 | European Pat. Off. |
| WO 94/01160 | 1/1994 | WIPO |

OTHER PUBLICATIONS

*International Plastics Selector—Plastics Digest*, 1994 edition, p. A–22.

*Primary Examiner*—John D. Yasko

[57] ABSTRACT

A balloon dilatation having a relatively stiff proximal catheter shaft which is formed at least in part of an engineering thermoplastic polymer material with a tensile strength of at least about 10,000 psi, an elongation of at least 50% and a tensile modulus of at least 300,000 psi. The polymer is preferably an aromatic polymer, and particularly polyetheretherketone.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–6 is confirmed.

New claims 7–17 are added and determined to be patentable.

*7. The balloon dilatation catheter of claim 1, wherein the polymeric material is a polyetheretherketone.*

*8. The balloon dilatation catheter of claim 4, wherein the polymeric material is a polyetheretherketone.*

*9. The balloon dilatation catheter of claim 5, wherein the polymeric material is a polyetheretherketone.*

*10. The balloon dilatation catheter of claim 6, wherein the polymeric material is a polyetheretherketone.*

*11. The balloon dilatation catheter of claim 1, wherein the proximal catheter shaft portion includes an outer tubular member made of the polymeric material.*

*12. The balloon dilatation catheter of claim 11, wherein the proximal material is a polyetheretherketone.*

*13. The balloon dilatation catheter of claim 5, wherein the outer tubular member is made of the polymeric material.*

*14. The balloon dilatation catheter of claim 13, wherein the polymeric material is a polyetheretherketone.*

*15. The balloon dilatation catheter of claim 1, wherein:*

*A. the polymeric material is a polyetheretherketone having a tensile strength greater than about 14,000 psi, an elongation greater than about 60* and a tensile modulus greater than about 400,000 psi; and

*B. the proximal catheter shaft portion has an outer tubular member and an inner tubular member which is disposed within the outer tubular member and which defines with the outer tubular member the first inner lumen extending therein, at least one of the inner and the outer tubular members being formed of the polyetheretherketone.*

*16. The balloon dilatation catheter of claim 1 sized and having the flexibility and pushability required for use as a dilatation catheter for percutaneous transluminal coronary angioplasty.*

*17. The balloon dilatation catheter of claim 16, wherein the polymeric material is a polyetheretherketone.*

* * * * *

(12) EX PARTE REEXAMINATION CERTIFICATE (7283rd)
United States Patent
Ainsworth et al.

(10) Number: US 5,554,121 C2
(45) Certificate Issued: Dec. 29, 2009

(54) INTRALUMINAL CATHETER WITH HIGH STRENGTH PROXIMAL SHAFT

(75) Inventors: Robert D. Ainsworth, Scotts Valley, CA (US); Tai C. Cheng, Mountain View, CA (US); Lawrence D. Wasicek, Sunnyvale, CA (US)

(73) Assignee: Advanced Cardiovascular Systems, Inc., Santa Clara, CA (US)

Reexamination Request:
No. 90/004,946, Mar. 23, 1998

Reexamination Certificate for:
Patent No.: 5,554,121
Issued: Sep. 10, 1996
Appl. No.: 08/280,210
Filed: Jul. 25, 1994

Reexamination Certificate B1 5,554,121 issued Jul. 14, 1998

(51) Int. Cl.
*A61M 29/02* (2006.01)
*A61M 25/00* (2006.01)
*A61L 29/06* (2006.01)
*A61L 29/00* (2006.01)
*A61L 29/14* (2006.01)

(52) U.S. Cl. .................. 604/103.1; 604/96.01; 604/524
(58) Field of Classification Search .... 604/96.01–103.1, 604/523, 524, 525, 264, 532; 606/192, 194
See application file for complete search history.

(56) References Cited

U.S. PATENT DOCUMENTS

| | | | | |
|---|---|---|---|---|
| 4,276,250 A | * | 6/1981 | Satchell et al. | 264/167 |
| 4,277,432 A | * | 7/1981 | Woinowski | 264/171.24 |
| 4,464,176 A | * | 8/1984 | Wijayarathna | 604/524 |
| 4,499,041 A | * | 2/1985 | Hahn et al. | 264/171.27 |
| 4,680,156 A | * | 7/1987 | Collier | 264/174.11 |
| 4,973,305 A | * | 11/1990 | Goltzer | 604/509 |
| 5,063,018 A | * | 11/1991 | Fontirroche et al. | 264/514 |
| 5,078,700 A | * | 1/1992 | Lambert et al. | 604/264 |
| 5,139,496 A | | 8/1992 | Hed | 606/23 |
| 5,221,728 A | | 6/1993 | Bennett et al. | |
| 5,259,839 A | | 11/1993 | Burns | 604/99 |
| 5,270,086 A | | 12/1993 | Hamlin | |
| 5,312,356 A | * | 5/1994 | Engelson et al. | 604/164.13 |
| 5,316,706 A | | 5/1994 | Muni et al. | |
| 5,344,400 A | | 9/1994 | Kaneko et al. | 604/96 |
| 5,423,754 A | | 6/1995 | Cornelius et al. | 604/103 |
| 5,531,715 A | | 7/1996 | Engelson et al. | 604/265 |
| 5,540,937 A | | 8/1996 | Chee | 604/280 |

FOREIGN PATENT DOCUMENTS

EP 0 452 595 A1 10/1991
WO WO 94/01160 1/1994

OTHER PUBLICATIONS

*International Plastics Selector–Plastics Digest*, 1994 edition 15, 2 pages.
*Plastics Extrusion Technology Handbook*, Second Edition, 1989, pp. 185–187.
Talbott et al., "The Effects of Crystallinity on the Mechanical Properties of PEEK Polymer and Graphite Fiber Reinforced PEEK", *Journal of Composite Materials*, vol. 21, Nov. 1987, pp. 1056–1081.
Cebe et al., "Effect of Thermal History on Mechanical Properties of Polyetheretherketone below the Glass Transition Temperature", *Journal of Applied Polymer Science*, vol. 33 (1987), pp. 487–503.
Coillier et al., "Processing Conditions and Properties of Semicrystalline Polymers, I: Effect of Mechanical Properties of a Chlorinated Polyether", *Polymer Engineering and Science*, vol. 11, No. 6, Nov. 1971, pp. 452–462.
*Victrex PEEK Properties and Processing*, Product Brochure of ICI Advanced Materials (1990), pp. 39–40.

* cited by examiner

*Primary Examiner*—Nicholas D Lucchesi

(57) ABSTRACT

A balloon dilatation having a relatively stiff proximal catheter shaft which is formed at least in part of an engineering thermoplastic polymer material with a tensile strength of at least about 10,000 psi, an elongation of at least 50% and a tensile modulus of at least 300,000 psi. The polymer is preferably an aromatic polymer and particularly polyetheretherketone.

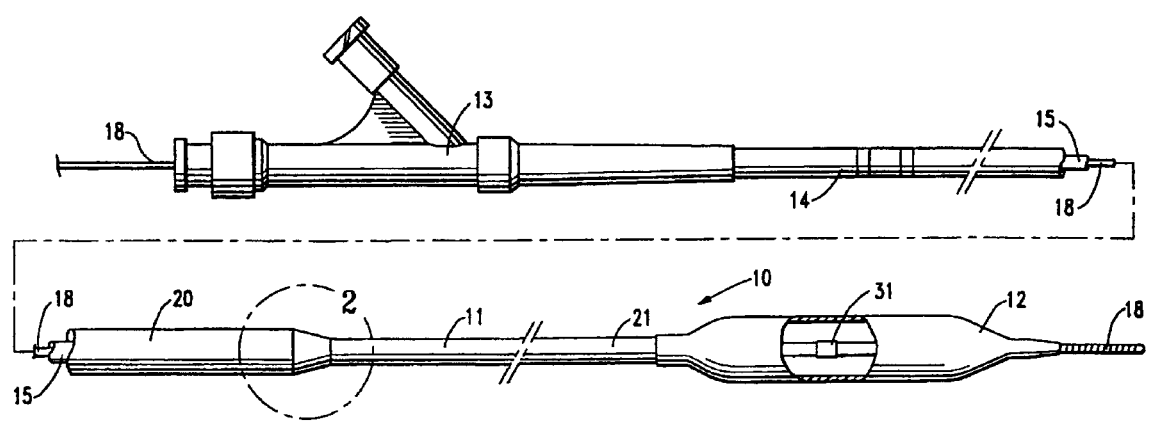

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–17 are cancelled.

* * * * *